United States Patent [19]

Brookhart et al.

[11] Patent Number: 5,099,061

[45] Date of Patent: Mar. 24, 1992

[54] RHODIUM-CATALYZED OLEFIN DIMERIZATION

[75] Inventors: Maurice S. Brookhart, Chapel Hill, N.C.; Sylviane Sabo-Etienne, Castanet Tolosan, France

[73] Assignee: The University of North Carolina at Chapel Hill, Chapel Hill, N.C.

[21] Appl. No.: 580,919

[22] Filed: Sep. 11, 1990

[51] Int. Cl.$^5$ .................. C07C 67/00; C07C 55/00; C07F 15/00

[52] U.S. Cl. .................. 560/202; 562/590; 556/7; 556/14; 556/136; 502/155; 502/161; 502/162; 502/169; 585/510; 585/511; 585/531

[58] Field of Search .............. 560/202; 556/7, 14, 556/136; 562/590, 599; 502/155, 161, 162, 169; 585/510, 511, 531

[56] References Cited

U.S. PATENT DOCUMENTS

| | | | |
|---|---|---|---|
| 3,013,066 | 12/1961 | Alderson | 260/486 |
| 3,636,122 | 1/1972 | Cramer et al. | 260/680 B |
| 4,594,447 | 6/1986 | Wilke et al. | 560/202 |
| 4,638,084 | 1/1987 | Singleton | 560/202 |
| 4,692,548 | 9/1987 | Drent | 560/202 |
| 4,786,623 | 11/1988 | Grenowillet et al. | 502/164 |
| 4,889,949 | 12/1989 | Grenowillet et al. | 560/202 |

FOREIGN PATENT DOCUMENTS 1214443  12/1970  United Kingdom ............... 560/202

OTHER PUBLICATIONS

T. Alderson et al., *Journal of the American Chemical Society* 87, No. 24, 5638 (1965).
M. Brookhart and D. Lincoln, *Journal of the American Chemical Society* 110, 8719 (1988).
W. Nugent and R. McKinney, *Journal of Molecular Catalysts* 29, 65 (1985).

*Primary Examiner*—Jose G. Dees
*Assistant Examiner*—Porfirio Nazario
*Attorney, Agent, or Firm*—Bell, Seltzer, Park & Gibson

[57] ABSTRACT

A process is disclosed for preparing functionalized linear olefins by dimerizing terminal olefins in the presence of a cationic rhodium compound. Novel rhodium compounds useful in this process are also disclosed.

16 Claims, No Drawings

RHODIUM-CATALYZED OLEFIN DIMERIZATION

This work was supported in part by National Science Foundation Grant Number CHE-8705534. The government may have certain rights to this invention.

FIELD OF THE INVENTION

This invention relates to a process for the rhodium-catalyzed linear dimerization of terminal olefins.

BACKGROUND OF THE INVENTION

The dimerization and codimerization of α-olefinic compounds in the presence of a group VIII noble metal salt is disclosed by Alderson (U.S. Pat. No. 3,013,066). The dimerization and codimerization of alkenes and alkyl acrylates in the presence of rhodium trichloride is disclosed by Alderson et al. (J. Amer. Chem. Soc. 1965, 87, 5638-5645).

Nugent et al. (J. Molecular Catalysis 1985, 29, 65-76) disclose a process for the linear dimerization of alkyl acrylates using chlorobis(ethylene)rhodium(I) dimer in combination with a Lewis acid promoter and a proton source.

Singleton (U.S. Pat. No. 4,638,084) discloses a process for dimerizing a lower alkyl acrylate or a lower alkyl methacrylate to the corresponding dialkyl hexenedioates and dialkyl 2,5-dimethylhexenedioates by contact with a catalyst prepared by reacting chlorobis(ethylene)rhodium(I) dimer and silver tetrafluoroborate.

Brookhart et al. (J. Amer. Chem. Soc. 1988, 110, 8719-8720) disclose the use of a cationic rhodium catalyst containing a pentamethylcyclopentadienyl ligand in the dimerization of ethylene to butenes.

SUMMARY OF THE INVENTION

This invention provides a process for preparing functionalized linear olefins which comprises reacting a first olefin, $H_2C=CR^1R^2$, with a second olefin, $H_2C=CR^3R^4$, in the presence of a cationic rhodium compound, $[L^1RhL^2L^3R]^+X^-$; wherein $R^1$ is selected from the group consisting of H and $C_1-C_{10}$ alkyl;

$R^2$ is selected from the group consisting of H, $C_1-C_{10}$ alkyl, phenyl, $C_7-C_{12}$ alkyl-substituted phenyl, $-COOR^5$, $-C(O)NR^6R^7$, and $-C(O)H$;

$R^3$ is selected from the group consisting of H and $C_1-C_{10}$ alkyl;

$R^4$ is selected from the group consisting of $-COOR^8$, $-C(O)NR^9R^{10}$, and $-C(O)H$;

$R^5$ and $R^8$ are independently selected from the group consisting of $C_1-C_{10}$ alkyl;

$R^6$, $R^7$, $R^9$, and $R^{10}$ are independently selected from the group consisting of H and $C_1-C_{10}$ alkyl;

$L^1$ is an anionic pentahapto ligand;

$L^2$ and $L^3$ are neutral 2-electron donor ligands;

R is selected from the group of H, $C_1-C_{10}$ alkyl, $C_6-C_{10}$ aryl, and $C_7-C_{10}$ aralkyl ligands;

$X^-$ is a non-coordinating anion; and wherein two or three of $L^2$, $L^3$ and R are optionally connected.

This invention also provides novel compounds, I and II, which are useful in the process of this invention,

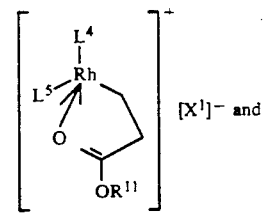

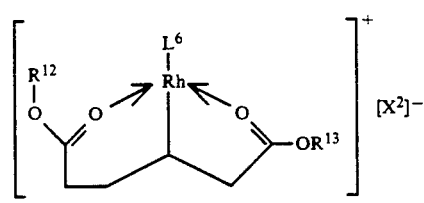

where $L^4$ is an anionic pentahapto ligand;

$L^5$ is a neutral 2-electron donor ligand;

$R^{11}$ is selected from the group of $C_1-C_{10}$ alkyl;

$[X^1]^-$ is a non-coordinating anion;

$L^6$ is an anionic pentahapto ligand;

$R^{12}$ and $R^{13}$ are independently selected from the group consisting of $C_1-C_{10}$ alkyl; and $[X^2]^-$ is a non-coordinating anion.

DETAILED DESCRIPTION OF THE INVENTION

The process of this invention can be used to homodimerize or codimerize functionalized terminal olefins in a linear, tail-to-tail fashion, or to dimerize functionalized terminal olefins with terminal alkenes. The products of the process of this invention are linear, functionalized olefins in which a carbon-carbon bond has been formed between the methylene carbons of the olefin reactants. Specific examples of useful products include dialkyl hexenedioates, which are precursors to adipic acid.

In the process of this invention, a linear functionalized olefin is prepared by reacting a first terminal olefin, $CH_2=CR^1R^2$, with a second terminal olefin, $CH_2=CR^3R^4$, in the presence of a cationic rhodium compound, $[L^1RhL^2L^3R]^+X^-$; wherein $R^1$ is selected from the group consisting of H and $C_1-C_{10}$ alkyl;

$R^2$ is selected from the group consisting of H, $C_1-C_{10}$ alkyl, phenyl, $C_7-C_{12}$ alkyl-substituted phenyl, $-COOR^5$, $-C(O)NR^6R^7$, and $-C(O)H$;

$R^3$ is selected from the group consisting of H and $C_1-C_{10}$ alkyl;

$R^4$ is selected from the group consisting of $-COOR^8$, $-C(O)NR^9R^{10}$, and $-C(O)H$;

$R^5$ and $R^8$ are independently selected from the group consisting of $C_1-C_{10}$ alkyl;

$R^6$, $R^7$, $R^9$, and $R^{10}$ are independently selected from the group consisting of H and $C_1-C_{10}$ alkyl;

$L^1$ is an anionic pentahapto ligand;

$L^2$ and $L^3$ are neutral 2-electron donor ligands;

R is selected from the group of H, $C_1-C_{10}$ alkyl, $C_6-C_{10}$ aryl, and $C_7-C_{10}$ aralkyl ligands;

$X^-$ is a non-coordinating anion, and wherein two or three of $L^2$, $L^3$ and R are optionally connected.

Suitable terminal olefins, $H_2C=CR^1R^2$, include: ethylene; terminal alkenes containing 3-12 carbon atoms, e.g., propene, 1-butene, isoprene, 1-pentene, 1-hexene, and 1-heptene; styrene; 4-methylstyrene; alkyl acrylates, where the alkyl group contains 1-10 carbon atoms, e.g., methyl acrylate and ethyl acrylate; methyl methacrylate; acrylamide; methacrylamide; N-alkyl acrylamides, where the alkyl group contains 1-10 carbon atoms, e.g., N-methylacrylamide; N-methyl methacrylamide; N,N-dialkyl acrylamides, where the alkyl groups contain 1-10 carbon atoms, e.g., N,N-dimethylacrylamide; acrolein; and methacrolein.

Suitable functionalized terminal olefins, $H_2C=CR^3R^4$, include: alkyl acrylates, where the alkyl group contains 1-10 carbon atoms, e.g., methyl acrylate and ethyl acrylate; methyl methacrylate; acrylamide; methacrylamide; N-alkyl acrylamides, where the alkyl group contains 1-10 carbon atoms, e.g., N-methylacrylamide; N-methyl methacrylamide; N,N-dialkyl acrylamides, where the alkyl groups contain 1-10 carbon atoms, e.g., N,N-dimethylacrylamide; acrolein; and methacrolein.

Preferably, $H_2C=CR^1R^2$ is ethylene, propylene, styrene, methyl acrylate, ethyl acrylate, acrolein, or N,N-dimethyl acrylamide. Preferably, $H_2C=CR^3R^4$ is methyl acrylate, ethyl acrylate, acrolein, or N,N-dimethyl acrylamide. More preferably, $H_2C=CR^1R^2$ is ethylene, styrene, methyl acrylate or ethyl acrylate and $H_2C=CR^3R^4$ is methyl acrylate or ethyl acrylate. Most preferably, $H_2C=CR^1R^2$ and $H_2C=CR^3R^4$ are both either methyl acrylate or ethyl acrylate.

The terminal olefins, $H_2C=CR^1R^2$ and $H_2C=CR^3R^4$, can be chosen to be the same or different olefins to give, respectively, homodimers or codimers. The efficiency of the production of codimers may depend on the specific olefins chosen, and thus it may be necessary to use a large excess of one of the olefins to obtain the desired codimer.

The cationic rhodium compound used in the process of this invention can be formed in one of several ways. A particularly convenient route involves reacting a precursor, $L^1RhL^{2'}L^{3'}$, with an acid, $H^+X^-$, where $L^1$ is an anionic pentahapto ligand;

$L^{2'}$ and $L^{3'}$ are neutral, 2-electron donor ligands, or $L^{2'}$ and $L^{3'}$ are connected to form a neutral, 4-electron ligand; and $X^-$ is a non-coordinating anion.

For example, $Cp^*Rh(C_2H_4)_2$ reacts with $HBF_4$ to give $[Cp^*Rh(CH_2CH_2...H)(C_2H_4)]^+BF_4^-$, which is useful in the process of this invention. (Cp* is pentamethylcyclopentadienyl.) Similarly, compound Ia ($L^4$ is Cp*; $L^5$ is $P(OMe)_3$; $R^{11}$ is Me; and $[X^1]^-$ is $BF_4^-$) can be made by reacting $HBF_4$ with Cp* $Rh(P(OMe)_3)(CH_2=CH-CO_2Me)$. In these routes to cationic rhodium compounds, suitable acids, $H^+X^-$, include: $HBF_4$; $HPF_6$; $H_2SO_4$; $CF_3SO_3H$; $CF_3CO_2H$; and tetraarylboronic acids, e.g., $HBPh_4$ and $HB(3,5-bis(trifluoromethyl)phenyl)_4$.

Alternatively, $L^1RhL^{2'}(R)Y$, where Y is a halide and $L^1$, $L^{2'}$, and R are as defined above, can be reacted with a Lewis acid in the presence of an olefin to form a cationic rhodium compound which is useful in the process of this invention. For example, $Cp^*Rh(P(OMe)_3)(Me)Br$ could be reacted with $AgBF_4$ in the presence of methyl acrylate to give the desired cationic rhodium compound, $[Cp^*Rh(P(OMe)_3)(CH_2=CHCO_2Me)(Me)]^+BF_4^-$. In catalyst preparations of this type, suitable Lewis acids include: $Ag^+X^-$, $AlX''_3$, $BX''_3$, $FeX''_3$, and $SbX''_5$, where X'' is halide.

In a third general route, precursors such as $[L^1RhL^{2'}L^4]^-$, where $L^4$ is a π-allylic ligand and $L^1$ and $L^{2'}$ are as defined above, can be reacted with $H_2$ to give cationic rhodium compounds which are useful in the process of this invention. For example, compounds of the class $[Cp^*Rh(MeOC(O)CH_2CHCHCHCO_2Me)]^+X^-$ III,

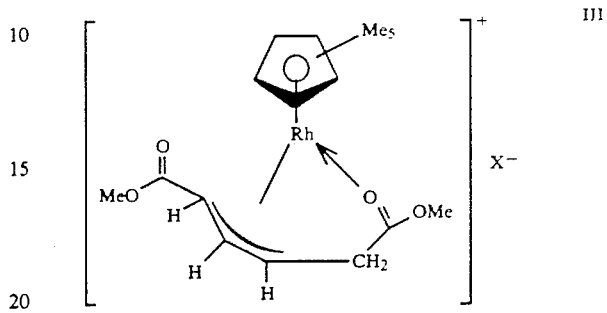

can be reacted with hydrogen to give cationic rhodium compounds which are useful in the process of this invention. A particularly useful precursor of this type is $[Cp^*Rh(MeOC(O)CN_2CHCHCHCO_2Me)]^+[B\{3,5-bis(trifluoromethyl)phenyl\}_4]^-$ IIIa.

In all of these rhodium compounds, suitable pentahapto ligands, $L^1$, $L^4$ and $L^6$ include: cyclopentadienyl and substituted derivatives of cyclopentadienyl containing 1-5 substitutents chosen from $C_1-C_4$ alkyl, trifluoromethyl, $C_6-C_{10}$ aryl, $COOR^{14}$ (where $R^{14}$ $C_1-C_4$ alkyl), and $C(O)R^{15}$ (where $R^{15}$ is $C_1-C_4$ alkyl); indenyl; fluorenyl; and carboranyl ligands such as (7,8,9,10,11-η)undecahydro-7,8-dicarbaundecaborato(2-) and (7,8,9,10,11-η)undecahydro-7,9-dicarbaundecaborato(2-). Preferably, $L^1$, $L^4$ and $L^6$ are alkyl-substituted derivatives of cyclopentadienyl; most preferably, $L^1$, $L^4$ and $L^6$ are pentamethylcyclopentadienyl (Cp*).

Suitable neutral, 2-electron donors, $L^2$, $L^3$, $L^{2'}$, $L^{3'}$, and $L^5$ include: carbon monoxide; alkyl-, aryl-, or mixed alkyl, arylphosphines (e.g., trimethylphosphine, triphenylphosphine, or diethylphenylphosphine); alkyl-, aryl-, or mixed alkyl, arylphosphites (e.g., trimethylphosphite, triphenylphosphite, or dimethylphenylphosphite); olefins (e.g., ethylene, propylene, 1-hexane, 1-octene, methyl acrylate, ethyl acrylate, or dimethyl hexendioate); nitriles (e.g., acetonitrile or benzonitrile); and the carbonyl groups of ketones (e.g., acetone) and esters (e.g., methyl acrylate). $L^2$ and $L^3$ can be the same or different, provided that if $L^2$ is a phosphine or phosphite, then $L^3$ is not a phosphine or phosphite. Similarly, $L^{2'}$ and $L^{3'}$ can be the same or different, but cannot both be phosphine or phosphite ligands. Preferred 2-electron donors include carbon monoxide, ethylene, trimethylphosphite, methyacrylate and dimethyl hexenedioate.

Alternatively, $L^2$ and $L^3$, or $L^{2'}$ and $L^{3'}$, may be connected to form a neutral 4-electron donoe ligand which contains two 2-electron-donor sites (olefin, phosphine, phosphite, nitrile or carbonyl groups). Suitable 4-electron-donor ligands of this type include: butadiene, 1,5-pentadiene, methyl vinyl ketone and acrylonitrile. Similarly, R and $L^2$ (or $L^{2'}$) can be connected, as in $[Cp^*Rh(CH_2CH_2...H)(C_2H_4)]^+BF_4^-$. Other suitable connected ligand systems include those in which $L^{2'}$ and $L^4$ are connected (as in compound III), and those in which R is connected $L^2$ and $L^3$ (as in $[Cp^*Rh\{CH(CH_2CH_2C(O)OMe)(CH_2-$ C(O)OMe)}]+X− (IIa), where L⁶ is Cp*, and $R^{12}$ and $R^{13}$ are Me).

Suitable R groups include: H; $C_1$-$C_{10}$ alkyl (e.g., methyl, ethyl, propyl, isoproyl, and butyl); $C_6$-$C_{10}$ aryl (e.g., phenyl, p-tolyl, and 3,5-dimethylphenyl); and $C_7$-$C_{10}$ aralkyl (e.g., benzyl, and —CH₂CH₂Ph).

[X]−, $[X^1]^-$, and $[X^2]^-$ are anions which do not coordinate to the cationic rhodium compounds, and include $BF_4^-$, $PF_6^-$, $CF_3SO_3^-$, and tetraaryl borates such as [B{3,5-bis(trifluoromethyl)phenyl}₄]− and $BPh_4^-$.

The novel compounds, I and II,

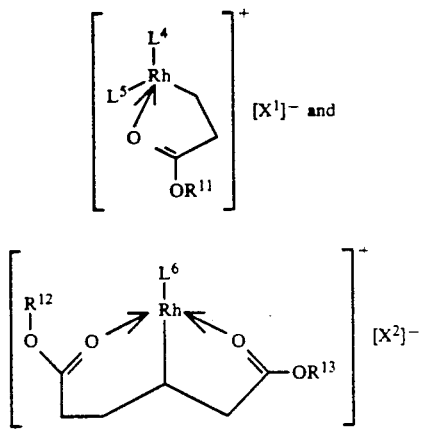

where
L⁴ is an anionic pentahapto ligand;
L⁵ is a neutral 2-electron donor ligand;
$R^{11}$ is selected from the group of $C_1$-$C_{10}$ alkyl;
$[X^1]^-$ is a non-coordinating anion;
L⁶ is an anionic pentahapto ligand;
$R^{12}$ and $R^{13}$ are independently selected from the group consisting of $C_1$-$C_{10}$ alkyl; and
$[X^2]^-$ is a non-coordinating anion
are among the preferred cationic rhodium compounds for use in this invention. Preferably $R^{11}$, $R^{12}$ and $R^{13}$ are methyl or ethyl, and $[X^2]^-$ is a non-coordinating anion such as $BF_4^-$, $PF_6^-$, $CF_3SO_3^-$, $BPh_4^-$, or [B{3,5-bis(-trifluoromethyl)phenyl}₄]−. $BF_4^-$ and [B{3,5-bis(trifluoromethy)phenyl}₄]− are most preferred. Most preferably, L⁵ is CO or trimethylphosphite.

Other preferred cationic rhodium compounds include:
[Cp*Rh(CH₂CH₂...H)(C₂H₄)]+X−; and
[Cp*Rh(P(OMe)₃)(CH₂=CHCO₂Me)(Me)]+X−,
where X− is a non-coordinating anion such as $BF_4^-$, $PF_6^-$, $CF_3SO_3^-$, $BPh_4^-$, or [B{3,5-bis(trifluoromethyl)-phenyl}₄]−. $BF_4^-$ and [B}3,5-bis(trifluoromethyl)phenyl}₄]− are most preferred.

The cationic rhodium compound can be prepared in situ in the presence of the olefin(s) to be dimerized, or it can be prepared separately and then added to the olefin(s).

The amount of cationic rhodium compound used is not critical. Molar ratios of olefin/Rh of 2/1 to 10,000/1 have been demonstrated, and higher ratios are possible.

Suitable solvents for the process of this invention are those in which the catalyst and olefin(s) are at least partially soluble, and which are not reactive under the process conditions. Suitable solvents include halocarbons, ethers, esters, and aromatic solvents. Preferred solvents include dichloromethane and diethyl ether. Alternatively, this process may be run in the absence of solvent, depending on the olefin(s). For example, the dimerization of methyl acrylate can easily be carried out in neat acrylate.

Suitable temperatures for the process of this invention range from about −100° C. to about 150° C., depending on the specific catalyst, olefin(s) and pressure. More preferably, the temperature is between 0° C. and 100° C.; most preferably between 20° C. and 80° C.

The process of this invention is not particularly sensitive to pressure, and pressures of 0.1 atm to 1,000 atm are suitable.

The process of this invention can be conducted in the presence of inert gases such as nitrogen, argon, helium, carbon dioxide and saturated hydrocarbons such as methane. In the preferred mode, the process is conducted in the presence of hydrogen, where the partial pressure of hydrogen is from about 0.1 atm to about 10 atm. Surprisingly, high yields of dimers are obtained and less than 3% saturated products are observed even under 1 atm hydrogen.

EXAMPLES

The following examples are provided to illustrate the invention and are not to be construed as limiting as invention. All preparativce manipulations were carried out using conventional Schlenk techniques. Methylene chloride was distilled from $P_2O_5$ under a nitrogen atmosphere. Methyl acrylate was stored under 4 Å molecular sieves. The rhodium complexes were prepared according to published procedures.

Reaction mixtures were analyzed by ¹H NMR spectroscopy. This method is advantageous since the fate of the rhodium species as well as the conversion of methyl acrylate into dimers can be monitored. The only dimers observed in all cases were linear, tail-to-tail dimers which included E- and Z—CH₃OC(O)—CH=CH—CH₂—CH₂—CO₂CH₃ (from here on referred to as E-2 and Z-2) and E—CH₃OC(O)—CH₂—CH=CH—CH₂CO₂CH₃ (from here on referred to as E-3). Normally, the E-2 isomer was the major isomer. Small amounts of E3 often appeared at the end of the reaction, probably due to isomerization of the E-2 and Z-2 isomers under the reaction conditions. The turnover number (TON) was defined as the number of moles or methyl acrylate consumed/mole of rhodium complex. The most efficient reactions were carried out under 1 atm H₂. Under these conditions very little (<3%) hydrogenation of methylacrylate occurs.

Examples 1-3 demonstrate relatively inefficient dimerization employing Cp*Rh(C₂H₄)(P(OMe)₃) as starting material. In all these examples the reaction was followed by ¹H NMR using NMR tubes sealed under vacuum.

EXAMPLE 1

HBF₄.Me₂O (32 μL, 0.287 mmol) is 5 mL diethyl ether was added at −30° C. to Cp*Rh(C₂H₄)(P(OMe)₃) (84 mg, 0.215 mmol) in 25 mL ether. The rhodium hydride salt [Cp*Rh(C₂H₄)(P(OMe)₃)H]+[BF₄]− precipitated immediately. The mixture was cooled to −80° C. and the ether solution was removed via cannula. The solid was washed with 2 portions of 5 mL of cold diethyl ether and dried under vacuum at low temperature.

Methyl acrylate (7.2 μL, 0.08 mmol) was added to an NMR tube at liquid nitrogen temperature containing [Cp*Rh(C₂H₄)(P(OMe)₃)H]+[BF₄]− (8 mg, 0.017 mmol) in 0.6 mL CD₂Cl₂. The NMR tube was then sealed under vacuum. The reaction was monitored by $^1$H NMR. A new complex Cp*Rh(CH$_2$CH$_2$CO$_2$Me)(P(OMe)$_3$) was obtained and slow dimerization of the methyl acrylate was observed. (50% conversion after 9 days)

EXAMPLE 2

The new complex [Cp*Rh(CH$_2$CH$_2$CO$_2$Me)(P(OMe)$_3$)]$^+$BF$_4^-$ (Ia) was prepared starting from [Cp*Rh(C$_2$H$_4$)(P(OMe)$_3$)H]$^+$[BF$_4$]$^-$ (140 mg, 0.293 mmol) and methyl acrylate (36 μL, 0.40 mmol) in 5 mL CH$_2$Cl$_2$. Then methyl acrylate (250 μL, 2.78 mmol) was added at room temperature. Slow dimerization was obtained: 17% conversion after 24 h and 58% after 12 days.

NMR data for [Cp*Rh(CH$_2$CH$_2$CO$_2$Me)(P(OMe)$_3$)]$^{30}$ BF$_4^-$ (Ia): $^1$H NMR (CD$_2$Cl$_2$, 400 MHz, 23° C.): δ3.79 (s, CO$_2$CH$_3$), 3.71 (d, $J_{P-H}$=12 Hz, P(OCH$_3$)$_3$), 2.9 (m, CH$_2$), 2.2 (m, CH$_2$), 1.67 (d, $J_{P-H}$=4 Hz, C$_5$(CH$_3$)$_5$).

$^{13}$C{$^1$H} NMR (CD$_2$Cl$_2$, 100 MHz, 23° C.): δ191.0 (s, CO$_2$CH$_3$), 101.2 (s, C$_5$(CH$_3$)$_5$), 55.6 (s, CO$_2$CH$_3$), 53.2 (d, $J_{P-C}$=4 Hz, P(OCH$_3$)$_3$), 39.1 (s, CH$_2$CO$_2$CH$_3$), 13.0 (t, $J_{Rh-C}$=$J_{P-C}$=18 Hz, RhCH$_2$), 9.3 (s, C$_5$(CH$_3$)$_5$).

EXAMPLE 3

Methyl acrylate (77 μL, 0.86 mmol) was added to [Cp*Rh(C$_2$H$_4$)(P(OMe)$_3$)H]$^+$[BF$_4$]$^-$ (12 mg, 0.025 mmol) prepared following the method described in Example 1. After 4 days, 50% conversion to dimers was obtained.

Examples 4-13 demonstrate very efficient dimerization employing Cp*Rh(C$_2$H$_4$)$_2$ as starting material. Only linear dimers were obtained.

EXAMPLE 4

HBF$_4$.OMe$_2$ (one drop) was added at −40° C. to Cp*Rh(C$_2$H$_4$)$_2$ (6 mg, 0.02 mmol) in 0.5 mL of CD$_2$Cl$_2$ in an NMR tube. After shaking, the tube was frozen at liquid nitrogen temperature. Methyl acrylate (250 μL, 2.78 mmol) was added and then the tube was sealed under vacuum at liquid nitrogen temperature. The reaction was then followed by NMR analysis at room temperature. After 45 min, 97% conversion to dimers was obtained. Dimers: E-2, 94%; Z-2, 4%; E-3, 2%.

EXAMPLE 5

HBF$_4$.OMe$_2$ (one drop) was added at −50° C. to Cp*Rh(C$_2$H$_4$)$_2$ (6 mg, 0.02 mmol) in 5 mL of CH$_2$Cl$_2$ in a 100 mL Schlenk flask. Methyl acrylate (i.5 mL, 27.8 mmol) (degassed under N$_2$) was added at −50° C. The mixture was then stirred at 0° C. The reaction was followed by NMR by withdrawing 50 μL of the mixture and adding it to 0.5 mL of CD$_2$Cl$_2$. After 20 h at 0° C., 63% conversion to dimers was obtained. Dimers: E-2, 86%, Z-2, 14%. TON=876.

EXAMPLE 6

The procedure described in Example 5 was repeated, except that the mixture was kept in a water bath at room temperature. After 3.83 h, 67% conversion to dimers was obtained. Dimers: E-2, 85%; Z-2, 18%. TON=931.

In Examples 7-11 and 13, HBPh$_4$** indicates HB[3,5-bis(trifluoromethyl)phenyl]$_4$.

EXAMPLE 7

HBPh$_4$** .(Et$_2$O)$_2$ (29 mg, 0.029 mmol) was added to Cp*Rh(C$_2$H$_4$)$_2$ (6 mg, 0.020 mmol) in 5 mL CH$_2$Cl$_2$ at 0° C. Methyl acrylate (3 mL, 33.3 mmol) was added at 0° C. and after 5 min the Schlenk flask was kept at room temperature in a water bath. Results are presented in the following table.

| Time (h) | % Conversion to dimers |
|---|---|
| 0.25 | 5 |
| 1 | 16 |
| 3 | 45 |
| 6 | 62 |
| 24 | 75 |

At 24 h, dimers were: E-2, 89%; Z-2, 11%. TON=1249.

EXAMPLE 8

This example shows that the presence of a solvent is not necessary.

HBPh$_4$**.(Et$_2$O)$_2$ (49 mg, 0.048 mmol) in 2 mL of diethyl ether was added at 0° C. to Cp*Rh(C$_2$H$_4$)$_2$ (10 mg, 0.034 mmol) in 2 mL of diethyl ether. After stirring 7 min, the mixture was evaporated to dryness at 0° C. under vacuum. Then methyl acrylate (8 mL, 88.9 mmol) was added at 0° C. to the remaining solid. After stirring 5 min, the Schlenk flask was kept in a water bath at room temperature. 47% conversion was obtained: E-2, 88%; Z-2, 12%. TON=1229.

EXAMPLE 9

This example shows that dimerization occurs at a temperature as low as −80° C.

HBPh$_4$**.(Et$_2$O)$_2$ (38 mg, 0.037 mmol) in 0.3 mL CD$_2$Cl$_2$ was added at 0° C. to Cp*Rh(C$_2$H$_4$)$_2$ (7 mg, 0.024 mmol) in 0.5 mL CD$_2$Cl$_2$ in an NMR tube. After cooling to −80° C., methyl acrylate (20 μL, 0.222 mmol) was added, and the tube was shaken just before its introduction into the NMR probe. Dimerization was observed at −80° C., but the reaction was very slow.

In Examples 10-13, the reactions were performed using N$_2$ and H$_2$ atmospheres.

EXAMPLE 10

HBPh$_4$**.(Et$_2$O)$_2$ (49 mg, 0.048 mmol) in 2 mL CH$_2$Cl$_2$ was added at 0° C. to Cp*Rh(C$_2$H$_4$)$_2$ (10 mg, 0.034 mmol) in 10 mL CH$_2$Cl$_2$. After stirring 10 min, methyl acrylate (8 mL, 88.9 mmol) was added to the mixture. The Schlenk flask was then kept at room temperature in a water bath. After 4 h reaction under N$_2$ atmosphere, 36% conversion to dimers was obtained. At this point, the mixture was divided into two fractions: one fraction was kept under N$_2$ and 47% conversion was finally obtained. H$_2$ was bubbled through the second fraction for 1 h, and 95% conversion to dimers was finally obtained. TON=2483 (H$_2$ atmosphere).

EXAMPLE 11

HBPh$_4$**.(Et$_2$O)$_2$ (50 mg, 0.049 mmol) in 1.5 mL CH$_2$Cl$_2$ was added at 0° C. to Cp*Rh(C$_2$H$_4$)$_2$ (10 mg, 0.034 mmol) in 2.5 mL CH$_2$Cl$_2$. After stirring 10 min, methyl acrylate (20 mL, 222.3 mmol) was added to the solution. The Schlenk flask was then kept at room temperature in a water bath under H$_2$ atmosphere. The results are reported in the following table:

| Time (h) | % Conversion to dimers |
|---|---|
| 4.33 | 14 |
| 22.33 | 68 |

| Time (h) | % Conversion to dimers |
|---|---|
| 48 | >99.9 |

At 48 h, TON=6538. Turnover rate=3.5 mol $CH_2=CHCO_2Me/mol(Rh)/min$ at 25° C. Dimers: E-2, 95%; Z-2, 3%; E-3, 2%.

EXAMPLE 12

One drop of $HBF_4.Me_2O$ was added at −40° C. to $Cp*Rh(C_2H_4)_2$ (10 mg, 0.034 mmol) in 10 mL of $CH_2Cl_2$. Methyl acrylate (8 mL, 88.9 mmol) was added to the mixture, and the mixture was then heated to 40°–50° C. under an $H_2$ atmosphere. (The Schlenk flask was equipped with a water condenser.) The reaction was only monitored for 4 h and at that point, 69% conversion was obtained.

Turnover rate=7.5 mol $CH_2=CHCO_2Me/mol(Rh)/min$ at 40° C.

EXAMPLE 13

$HBPh_4**.(Et_2O)_2$ (50 mg, 0.049 mmol) in 3 mL $CH_2Cl_2$ was added at 0° C. to $Cp*Rh(C_2H_4)_2$ (10 mg, 0.034 mmol) in 3 mL $CH_2Cl_2$. After stirring 10 min, methyl acrylate (20 mL, 222.3 mmol) was added to the solution. The Schlenk flask was then kept at room temperature in a water bath under $H_2$ atmosphere. The results are reported in the following table:

| Time (h) | % Conversion to dimers |
|---|---|
| 2 | 12 |
| 3.25 | 20 |
| 4.33 | 27 |
| 5.33 | 33 |
| 7.75 | 47 |
| 9.75 | 59 |
| 11.50 | 67 |
| 12.92 | 75 |
| 14.83 | 84 |
| 16.75 | 91 |
| 18.50 | 95 |
| 20.33 | 97 |

After 11.50 h, the mixture was frozen in dry ice/acetone overnight. Just after thawing, no change was noticed in the monomer/dimer ratio and the reaction was then monitored in the same manner as before freezing. After 36 h at room temperature, >99.9% conversion was obtained, giving a TON=6538. (No data points were taken between 20.33 and 36 h.) Turnover rate=6.6 mol $CH_2=CHCO_2Me/mol(Rh)/min$ at 25° C. (over the initial 10 h period). Dimers: E-2, 94%; Z-2, 5%; E-3, 1%.

EXAMPLE 14

The procedure described in Example 13 was repeated, except that the mixture was heated to 60° C. under $H_2$ atmosphere.

After 3 h, 94% conversion was obtained. An additional 20 mL of methyl acrylate was added, and after 22 h, 99% conversion was obtained at 60° C., giving a TON=13,000. Turnover rate=65 mol $CH_2=CHCO_2Me/mol(Rh)/min$ at 60° C. (over the initial (1 h) period). Products: Dimers (98%): E-2, 93%; Z-2, 6%; E-3, 1%; Methyl propionate (2%).

EXAMPLE 15

This example describes the synthesis (2 methods) and the characterization of the new complexes $[Cp*RhCH(CH_2CO_2Me)(CH_2CH_2CO_2Me)]^+[BPh_4**]^-$ (IIb) and $\{Cp*Rh(\eta^3\text{-MeOC}(O)CH_2CHCHCO_2Me)\}^+[BPh_4**]^-$ (IIIb).

Method 1: $HBPh_4**.(Et_2O)_2$ (218 mg, 0.215 mmol) in 3 mL $CH_2Cl_2$ was added at 0° C. to $Cp*Rh(C_2H_4)_2$ (49 mg, 0.167 mmol) in 7 mL $CH_2Cl_2$. After stirring 10 min, $MeOC(O)CH=CHCH_2CH_2CO_2Me$ (200 μL) was added to the mixture. After stirring overnight at room temperature, the solution was evaporated to dryness. The residue was washed with hexane to eliminate the dimer. The two complexes (IIb) and (IIIb) were separated by successive recrystallizations in diethyl ether/hexane and isolated as orange crystals.

Method 2: $HBPh_4**.(Et_2O)_2$ (171 mg, 0.169 mmol) in 3 mL $CH_2Cl_2$ was added at 0° C. to $Cp*Rh(C_2H_4)_2$ (39 mg, 0.133 mmol) in 7 mL $CH_2Cl_2$. After stirring 10 min, methyl acrylate (240 μL, 2.668 mmol) was added to the mixture. After stirring overnight at room temperature, the solution was evaporated to dryness. The residue was washed with hexane to eliminate excess dimer. The two complexes (IIb) and (IIIb) were separated by successive recrystallizations in diethyl ether/hexane and isolated as orange crystals.

NMR data for $[Cp*RhCH(CH_2CO_2Me)(CH_2CH_2CO_2Me)]^+[BPh_4**]^-$ (IIb):

$^1H$ NMR (400 MHz, $CD_2Cl_2$, 23° C.): δ7.72 (Ph, 8H), 7.56 (Ph, 4H), 3.93 (s, $CO_2CH_3$), 3.84 (s, $CO_2CH_3$), 3.35 (m, broad, Ha), 3.00 (dd, $J_{Ha-Hb}$ or c=9 Hz, $J_{Hb-Hc}$=19 Hz, Hb or c), 2.68 (d, $J_{Hb-Hc}$=19 Hz, Hc or b), 2.40 (ddd, J=3, 7 and 19 Hz, Hf or g), 2.15 (ddd, J=3, 9 and 19 Hz, Hg or f), 1.68 (m, Hd or e), 1.53 (s, $C_5(CH_3)_5$), 1.52 (m, He or d).

$^{13}C$ NMR (100 MHz, $CD_2Cl_2$, 23° C.): δ190.4 (s, $CO_2CH_3$), 183.0 (s, $CO_2CH_3$), 162.1 (q, $J_{C-B}$=50 Hz, C1'), 135.2 (d, $J_{C-H}$=157.5 Hz, C2' and C6'), 129.3 (q, $^2J_{C-F}$=32 Hz, C3' and C5'), 125.0 (q, $J_{C-F}$=273 Hz, $CF_3$) 117.9 (dq, $J_{C-H}$=163 Hz, $^3J_{C-F}$=4 Hz, C4'), 94.6 (d, $J_{C-Rh}$=8 Hz, $C_5(CH_3)_5$), 55.7 (q, $J_{C-H}$=150 Hz, $CO_2CH_3$), 54.9 (q, $J_{C-H}$=150 Hz, $CO_2CH_3$), 44.8 (t, $J_{C-H}$=130 Hz, $CH_2$), 38.7 (dd, $J_{C-Rh}$=23 Hz, $J_{C-H}$=140 Hz, Rh-CH), 31.6 (t, $J_{C-H}$=130 Hz, $CH_2$), 29.9 (t, $J_{C-H}$=130, $CH_2$), 8.9 (q, $J_{C-H}$=129 Hz, $C_5(CH_3)_5$).

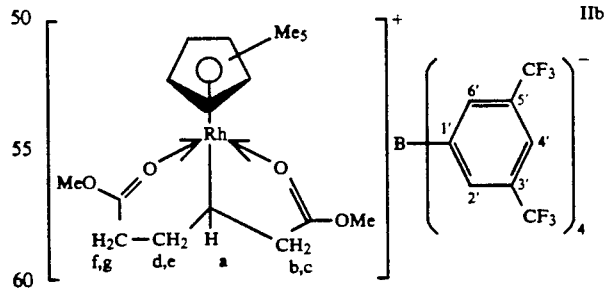

NMR data for $[Cp*Rh(\eta^3\text{-MeOC}(O)CH_2CHCHCH CO_2Me)]^+[BPh_4**]^-$ (IIIb):

$^1H$ NMR (400 MHz, $CD_2Cl_2$, 23° C.): δ7.72 (Ph, 8H), 7.56 (Ph, 4H), 5.49 (ddd, $J_{Ha-Hb}$=11 Hz, $J_{Hc-Hb}$=8 Hz, $J_{Rh-Hb}$=2 Hz, Hb), 4.70 (ddd, $J_{Hb-Hc}$=8 Hz, $J_{Hc-Hd}$=7.5 Hz, $J_{Hc-He}$=2 Hz, Hc), 3.85 (s, $CO_2CH_3$), 3.82 (s, $CO_2CH_3$), 3.42 (dd, $J_{Hd-Hc}$=7.5 Hz, $J_{Hd-He}$=21

Hz, Hd), 3.11 (d, $J_{Ha-Hb}=11$ Hz, Ha), 2.61 (dd, $J_{He-Hd}=21$ Hz, $J_{He-Hc}=2$ Hz, He), 1.70 (s, $C_5(CH_3)_5$).

$^{13}C\{^1H\}$ NMR (100 MHz, $CD_2Cl_2$, 23° C.): δ186.8 (s, C5), 170.0 (s, C6), 162.1 (q, $J_{C-B}=50$ Hz, C1'), 135.2 (s, C2' and C6'), 129.3 (q, $^2J_{C-F}=32$ Hz, C3' and C5'), 125.0 (q, $J_{C-F}=273$ Hz, CF3), 117.9 (q, $^3J_{C-F}=4$ Hz, C4'), 102.5 (d, $J_{C-Rh}=5$ Hz, C2), 101.3 (d, $J_{C-Rh}=7$ Hz, $C_5(CH_3)_5$), 71.6 (d, $J_{C-Rh}=9$ Hz, C3), 67.8 (d, $J_{C-Rh}=10$ Hz, C1), 56.5 (s, $OCH_3$), 52.5 (s, $OCH_3$), 36.5, (s, C4), 8.9 (s, $C_5(CH_3)_5$).

$^{13}C$ NMR (100 MHz, $CD_2Cl_2$, 23° C.): δ186.8 (s, C5), 170.0 (s, C6), 162.1 (q, $J_{C-B}=50$ Hz, C1'), 135.2 (d, $J_{C-H}=157.5$ Hz, C2' and C6'), 129.3 (q, $^2J_{C-F}=32$ Hz, C3' and C5'), 125.0 (q, $J_{C-F}=273$ Hz, CF3), 117.9 (dq, $J_{C-H}=163$ Hz, $^3J_{C-F}=4$ Hz, C4'), 102.5 (m, $J_{C-H}=170$ Hz, C2), 101.3 (d, $J_{C-Rh}=7$ Hz, $C_5(CH_3)_5$), 71.6 (m, $J_{C-H}=160$ Hz, C3), 67.8 (dt, $J_{C-H}=161$ Hz, $^1J_{C-Rh}=^2J_{C-Hb}=10$ Hz, C1), 56.5 (q, $J_{C-H}=151$ Hz, $OCH_3$), 52.5 (q, $J_{C-H}=148$ Hz, $OCH_3$), 36.5, (t, $J_{C-H}=130$ Hz, C4), 8.9 (q, $J_{C-H}=129$ Hz, $C_5(CH_3)_5$).

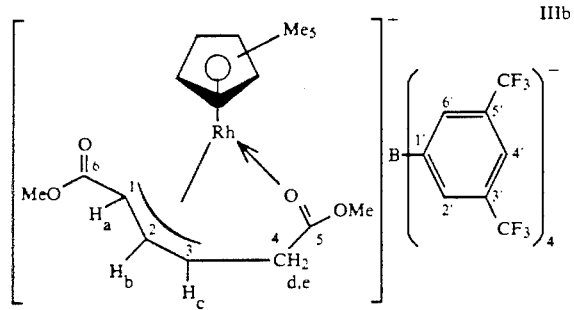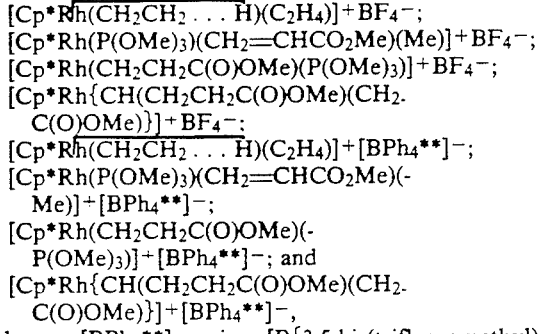

IIIb

We claim:

1. A process for preparing functionalized linear olefins which comprises reacting a first olefin, $H_2C=CR^1R^2$, with a second olefin, $H_2C=CR^3R^4$, in the presence of a cationic rhodium compound, $[L^1RhL^2L^3R]^+X^-$; wherein
   $R^1$ is selected from the group consisting of H and $C_1-C_{10}$ alkyl;
   $R^2$ is selected from the group consisting of H, $C_1-C_{10}$ alkyl, phenyl, $C_7-C_{12}$ alkyl-substituted phenyl, $—COOR^5$, $—C(O)NR^6R^7$, and $—C(O)H$;
   $R^3$ is selected from the group consisting of H and $C_1-C_{10}$ alkyl;
   $R^4$ is selected from the group consisting of $—COOR^8$, $—C(O)NR^9R^{10}$, and $—C(O)H$;
   $R^5$ and $R^8$ are independently selected from the group consisting of $C_1-C_{10}$ alkyl;
   $R^6$, $R^7$, $R^9$, and $R^{10}$ are independently selected from the group consisting of H and $C_1-C_{10}$ alkyl;
   $L^1$ is an anionic pentahapto ligand;
   $L^2$ and $L^3$ are neutral 2-electron donor ligands;
   R is selected from the group of H, $C_1-C_{10}$ alkyl, $C_6-C_{10}$ aryl, and $C_7-C_{10}$ aralkyl ligands;
   $X^-$ is a non-coordinating anion; and
   wherein two or three of $L^2$, $L^3$ and R are optionally connected.

2. A process according to claim 1 wherein said process is carried out between the temperatures of $-100°$ C. to 150° C.

3. A process according to claim 2 wherein said first olefin is selected from the group consisting of ethylene, propylene, styrene, methyl acrylate, ethyl acrylate, acrolein, and N,N-dimethyl acrylamide and said second olefin is selected from the group consisting of methyl acrylate, ethyl acrylate, acrolein, and N,N-dimethyl acrylamide.

4. A process according to claim 3 wherein $L^1$ is pentamethylcyclopentadienyl.

5. A process according to claim 4 in which said first olefin is selected from the group consisting of ethylene, styrene, methyl acrylate and ethyl acrylate, and said second olefin is selected from the group consisting of methyl acrylate and ethyl acrylate.

6. A process according to claim 5 in which said cationic rhodium compound is selected from the group consisting of:
$[Cp^*Rh(CH_2CH_2 \ldots H)(C_2H_4)]^+BF_4^-$;
$[Cp^*Rh(P(OMe)_3)(CH_2=CHCO_2Me)(Me)]^+BF_4^-$;
$[Cp^*Rh(CH_2CH_2C(O)OMe)(P(OMe)_3)]^+BF_4^-$;
$[Cp^*Rh\{CH(CH_2CH_2C(O)OMe)(CH_2-C(O)OMe)\}]^+BF_4^-$;
$[Cp^*Rh(CH_2CH_2 \ldots H)(C_2H_4)]^+[BPh_4^{**}]^-$;
$[Cp^*Rh(P(OMe)_3)(CH_2=CHCO_2Me)(Me)]^+[BPh_4^{**}]^-$;
$[Cp^*Rh(CH_2CH_2C(O)OMe)(P(OMe)_3)]^+[BPh_4^{**}]^-$; and
$[Cp^*Rh\{CH(CH_2CH_2C(O)OMe)(CH_2-C(O)OMe)\}]^+[BPh_4^{**}]^-$,
where $[BPh_4^{**}]^-$ is $[B\{3,5-bis(trifluoromethyl)phenyl\}_4]^-$.

7. A process according to claim 6 in which the partial pressure of hydrogen is 0.1 to 10 atm.

8. A process according to claim 7 in which said first olefin is methyl acrylate and said second olefin is methyl acrylate.

9. A process for preparing functionalized linear olefins which comprises reacting a first olefin, $H_2C=CR^1R^2$, said first olefin selected from the group consisting of ethylene, propylene, styrene, methyl acrylate, ethyl acrylate, acrolein, and N,N-dimethyl acrylamide, with a second olefin, $H_2C=CR^3R^4$, said second olefin selected from the group consisting of methyl acrylate, ethyl acrylate, acrolein, and N,N-dimethyl acrylamide, in the presence of a cationic rhodium compound, $[L^1RhL^2L^3R]^+X^-$, wherein:
   $R^1$ is selected from the group consisting of H and $C_1-C_{10}$ alkyl;
   $R^2$ is selected from the group consisting of H, $C_1-C_{10}$ alkyl, phenyl, $C_7-C_{12}$ alkyl-substituted phenyl, $—COOR^5$, $—C(O)NR^6R^7$, and $—C(O)H$;
   $R^3$ is selected from the group consisting of H and $C_1-C_{10}$ alkyl;
   $R^4$ is selected from the group consisting of $—COOR^8$, $—C(O)NR^9R^{10}$, and $—C(O)H$;
   $R^5$ and $R^8$ are independently selected from the group consisting of $C_1-C_{10}$ alkyl;
   $R^6$, $R^7$, $R^9$ and $R^{10}$ are independently selected from the group consisting of H and $C_1-C_{10}$ alkyl;
   $L^1$ is an anionic pentahapto ligand;
   $L^2$ and $L^3$ are neutral 2-electron donor ligands;
   R is selected from the group of H, $C_1-C_{10}$ alkyl, $C_6-C_{10}$ aryl, and $C_7-C_{10}$ aralkyl ligands;
   $X^-$ is a non-coordinating anion; and
   wherein two or three of $L^2$, $L^3$, and R are optionally connected, in the presence of hydrogen at a partial pressure of about 0.1 atm to about 10 atm.

10. A process according to claim 9, wherein said first olefin is selected from the group consisting of ethylene, propylene, styrene, methyl acrylate, and ethyl acrylate, and said second olefin is selected from the group consisting of methyl acrylate and ethyl acrylate.

11. A process according to claim 9, wherein said first olefin is selected from the group consisting of methyl acrylate and ethyl acrylate and said second olefin is selected from the group consisting of methyl acrylate and ethyl acrylate.

12. A process according to claim 9, wherein said first olefin is methyl acrylate and said second olefin is methyl acrylate.

13. A process according to claim 9, wherein said process is carried out between the temperatures of $-100°$ C. to $150°$ C.

14. A process according to claim 9, wherein said process is carried out between the temperatures of $20°$ C. and $80°$ C.

15. A process according to claim 9, wherein $L^1$ is pentamethylcyclopentadienyl.

16. A process according to claim 9, wherein said cationic rhodium compound is selected from the group consisting of:

$[Cp^*Rh(CH_2CH_2 \ldots H)(C_2H_4)]^+BF_4^-$;
$[Cp^*Rh(P(OMe)_3)(CH_2=CHCO_2Me)(Me)]^+BF_4^-$;
$[Cp^*Rh(CH_2CH_2C(O)OMe)(P(OMe)_3)]^+BF_4^-$.
$[Cp^*Rh\{CH(CH_2CH_2C(O)OMe)(CH_2C(O)OMe)\}]^+BF_4^-$;
$[Cp^*Rh(CH_2CH_2 \ldots H)(C_2H_4)]^+[BPh_4^{**}]^-$;
$[Cp^*Rh(P(OMe)_3)(CH_2=CHCO_2Me)(Me)]^+[BPh_4^{**}]^-$;
$[Cp^*Rh(CH_2CH_2C(O)OMe)(P(OMe)_3)]^+[BPh_4^{**}]^-$; and
$[Cp^*Rh\{CH(CH_2CH_2C(O)OMe)(CH_2C(O)OMe)\}]^+[BPh_4^{}]^-$, where $[BPh_4^{}]^-$ is $[B\{3,5\text{-bis(trifluoromethyl)phenyl}\}_4]^-$.

* * * * *

UNITED STATES PATENT AND TRADEMARK OFFICE
CERTIFICATE OF CORRECTION

PATENT NO. : 5,099,061

DATED : 24 March 1992

INVENTOR(S) : Maurice S. Brookhart, Sylviane Sabo-Etienne, Castanet Tolosan

It is certified that error appears in the above-identified patent and that said Letters Patent is hereby corrected as shown below:

Column 4, line 25, please change "CN$_2$" to --CH$_2$--.

Column 4, line 34 and 35, please change ")undecahydro" to --)-undecahydro --.

Column 4, line 46, please change "1-hexane" to --1-hexene--.

Column 4, line 58, please change "donoe" to --donor--.

Column 5, line 46, please change "fluoromethy)" to --fluoromethyl) --.

Column 6, line 25, please change "preparativce" to --preparative--.

Column 6, line 45, please change "of moles or" to --of moles of--.

Column 7, line 17, please change ")]$^{30}$ BF$_4$" to --)]$^+$ BF$_4$ --.

Column 7, line 22, please change "CO$_2$CH$_3$)" to --$\underline{C}$O$_2$CH$_3$)--.

Column 7, line 22, please change "C$_5$(" to --$\underline{C}_5$(--.

Column 7, line 22, please change "(s, CO$_2$CH$_3$)" to --(s, CO$_2\underline{C}$H$_3$)--.

Column 7, line 23, please change "(OCH$_3$)" to --(O$\underline{C}$H$_3$)--.

Column 7, line 23, please change "(s, CH$_2$" to --(s, $\underline{C}$H$_2$--.

Column 7, line 24, please change "RhCH$_2$), 9.3 (s, C$_5$(CH$_3$)$_5$)." to --Rh$\underline{C}$H$_2$), 9.3 (s, C$_5$($\underline{C}$H$_3$)$_5$). --.

UNITED STATES PATENT AND TRADEMARK OFFICE
CERTIFICATE OF CORRECTION

PATENT NO. : 5,099,061

DATED : 24 March 1992

INVENTOR(S) : Maurice S. Brookhart, Sylviane Sabo-Etienne, Castanet Tolosan

It is certified that error appears in the above-identified patent and that said Letters Patent is hereby corrected as shown below:

Column 7, line 50, please change "i.5" to --2.5--.

Column 10, line 39, please change "$CO_2CH_3$), 183.0 (s, $CO_2CH_3$)," to --$\underline{C}O_2CH_3$), 183.0 (s, $\underline{C}O_2CH_3$),--.

Column 10, line 43, please change "$C_5$" to --$\underline{C}_5$--.

Column 10, line 44, please change "$CO_2CH_3$)" to --$CO_2\underline{C}H_3$)--.

Column 10, line 45, please change "$CH_2$)," to --$\underline{C}H_2$),--.

Column 10, line 46, please change "CH), 31.6 (t, $J_{C-H}$=130 $H_z$, $CH_2$)" to --$\underline{C}H$), 31.6 (t, $J_{C-H}$=130 $H_z$, $\underline{C}H_2$)--.

Column 10, line 47, please change "$CH_2$), 8.9 (q. $J_{C-H}$=129 $H_z$, $C_5(CH_3)$" to --$\underline{C}H_2$), 8.9 (q. $J_{C-H}$=129 $H_z$, $C_5(\underline{C}H_3)$--.

Column 11, line 6, please change "$CF_3$)" to --$\underline{C}F_3$)--.

Column 11, line 9, please change "(s, $OCH_3$), 52.5 (s, $OCH_3$)" to --(s, $O\underline{C}H_3$), 52.5 (s, $O\underline{C}H_3$)--.

Column 11, line 10, please change "($CH_3$)" to --($\underline{C}H_3$)--.

Column 11, line 14, please change "$CF_3$)" to --$\underline{C}F_3$)--.

Column 11, line 16, please change "$C_5$" to --$\underline{C}_5$--.

Column 11, line 18 and 19, please change "$OCH_3$" to --$O\underline{C}H_3$--.

UNITED STATES PATENT AND TRADEMARK OFFICE
CERTIFICATE OF CORRECTION

PATENT NO. : 5,099,061

DATED : 24 March 1992

INVENTOR(S) : Maurice S. Brookhart, Sylviane Sabo-Etienne, Castanet Tolosan

It is certified that error appears in the above-identified patent and that said Letters Patent is hereby corrected as shown below:

Column 11, line 20, please change "($CH_3$)" to --($\underline{C}H_3$)--.

Signed and Sealed this

Twenty-first Day of September, 1993

Attest:

BRUCE LEHMAN

*Attesting Officer*  *Commissioner of Patents and Trademarks*